(12) United States Patent
Wietelmann et al.

(10) Patent No.: US 8,168,806 B2
(45) Date of Patent: *May 1, 2012

(54) BORON CHELATE COMPLEXES

(75) Inventors: Ulrich Wietelmann, Friedrichsdorf (DE); Uwe Lischka, Niedereschbach (DE); Klaus Schade, Wiesbaden (DE); Jan-Christoph Panitz, Frankfurt (DE)

(73) Assignee: Chemetall GmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/634,963

(22) Filed: Dec. 10, 2009

(65) Prior Publication Data

US 2010/0168476 A1 Jul. 1, 2010

Related U.S. Application Data

(63) Continuation of application No. 11/355,863, filed on Feb. 16, 2006, now Pat. No. 7,709,663, which is a continuation of application No. 10/467,220, filed as application No. PCT/EP02/01639 on Feb. 15, 2002, now abandoned.

(30) Foreign Application Priority Data

Feb. 22, 2001 (DE) .................. 101 08 592

(51) Int. Cl.
*C07D 311/00* (2006.01)
(52) U.S. Cl. ....................................... 549/213
(58) Field of Classification Search .................... 549/213
See application file for complete search history.

(56) References Cited

U.S. PATENT DOCUMENTS 7,527,899 B2 * 5/2009 Angell et al. ................ 429/303
7,709,663 B2 * 5/2010 Wietelmann et al. ......... 549/213

OTHER PUBLICATIONS

Angell et al. CAS: 136:56441, 2001.*

* cited by examiner

*Primary Examiner* — Rei-tsang Shiao
(74) *Attorney, Agent, or Firm* — Fulbright & Jaworski L.L.P.

(57) ABSTRACT

Boron chelate complexes of the general formula

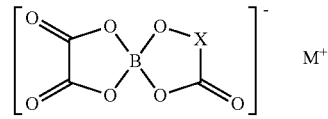

are described, where
X is either —C(R$^1$R$^2$)— or —C(R$^1$R$^2$)—C(=O)—, in which
R$^1$, R$^2$ independently of one another denote H, alkyl (with 1 to 5 C atoms), aryl, silyl or a polymer, and one of the alkyl radicals R$^1$ or R$^2$ may be bonded to a further chelatoborate radical,
or X denotes 1,2-aryl with up to two substituents S in the positions 3 to 6

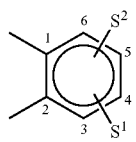

in which S$^1$, S$^2$ independently of one another denote alkyl (with 1 to 5 C atoms), fluorine or a polymer,
as well as M$^+$ denotes Li$^+$, Na$^+$, K$^+$, Rb$^+$, Cs$^+$ or [(R$^3$R$^4$R$^5$R$^6$)N]$^+$ or H$^+$,
where R$^3$, R$^4$, R$^5$, R$^6$ independently of one another denote H or alkyl with preferably 1 to 4 C atoms.

15 Claims, 1 Drawing Sheet

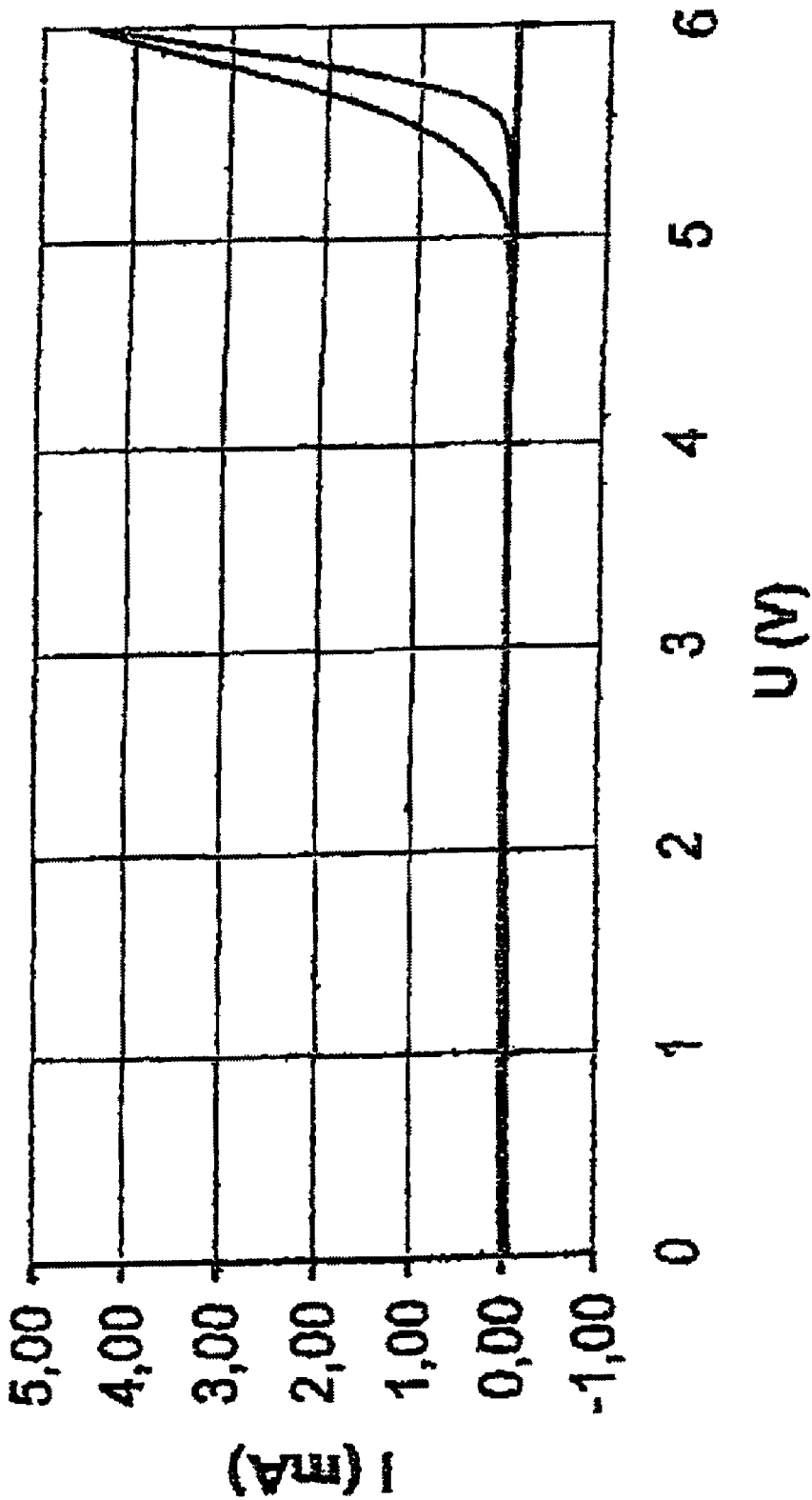

BORON CHELATE COMPLEXES

RELATED APPLICATIONS

This application is a continuation of U.S. Ser. No. 11/355,863 filed Feb. 16, 2006, now U.S. Pat. No. 7,709,663 herein incorporated by reference in its entirety, which is a continuation of U.S. Ser. No. 10/467,220 filed Sep. 23, 2003 abandoned, which is a §371 of PCT/EP02/01639 filed Feb. 15, 2002 which claims priority from DE WI 08 592.3 filed Feb. 22, 2001.

FIELD OF THE INVENTION

The present invention relates to boron chelate complexes, a process for their production as well as their use as electrolytes and as catalysts.

BACKGROUND OF THE INVENTION

Mobile electronics devices require increasingly more efficient and rechargeable batteries to provide an independent power supply. Besides nickel-cadmium and nickel-metal hydride batteries, specially rechargeable lithium batteries, which have a substantially higher energy density compared to nickel batteries, are suitable for this purpose. The systems available on the market have a terminal voltage of ca. 3 V; this relatively high potential means that water-based electrolyte systems cannot be used in lithium batteries. Instead, non-aqueous, mostly organic electrolytes (i.e. solutions of a lithium salt in organic solvents such as carbonates, ethers or esters) are used in liquid systems.

In the currently predominating battery design—lithium ion batteries with liquid electrolytes—practically exclusively lithium hexafluorophosphate ($LiPF_6$) is used as conducting salt. This salt satisfies the necessary preconditions for use in high-energy cells, i.e. it is readily soluble in aprotic solvents, leads to electrolytes with high conductivities, and has a high level of electrochemical stability. Oxidative decomposition occurs only at potential values greater than ca. 4.5 V. $LiPF_6$ has serious disadvantages however, which can mainly be attributed to a lack of thermal stability (it decomposes above ca. 130° C.). Also, on contact with moisture corrosive and poisonous hydrogen fluoride is released, which on the one hand complicates handling and on the other hand attacks and damages other battery components, for example the cathode.

Given this background, intensive efforts have been made to develop alternative conducting salts, and in particular lithium salts with perfluorinated organic radicals have been tested. These salts include lithium trifluoromethane sulfonate ("Litriflate"), lithium imides(lithium-bis(perfluoroalkylsulfonyl) imides) as well as lithium methides(lithium-tris(perfluoroalkylsulfonyl)methides). All these salts require relatively complicated production processes and are therefore relatively expensive, and have other disadvantages such as corrosiveness with respect to aluminium or poor conductivity.

Lithium organoborates have been investigated as a further class of compounds for use as conducting salt in rechargeable lithium batteries. On account of their low oxidation stability and safety considerations in the handling of triorganoboranes, their use for commercial systems is excluded however.

The lithium complex salts of the type $ABL_2$ (where A denotes lithium or a quaternary ammonium ion, B denotes boron and L denotes a bidentate ligand that is bound via two oxygen atoms to the boron atom) proposed in EP 698301 for use in galvanic cells represent a considerable step forward. The proposed salts, whose ligands contain at least one aromatic radical, however only have a sufficient electrochemical stability if the aromatic radical is substituted by electron-attracting radicals, typically fluorine, or if it contains at least one nitrogen atom in the ring. Such chelate compounds are not commercially available and can be produced only at high cost. The proposed products could therefore not penetrate the market.

Very similar boron compounds are proposed in EP 907217 as constituents in organic electrolytic cells. Compounds of the general formula LiBXX' are proposed as boron-containing conducting salt, where the ligands X and X' may be identical or different and each ligand contains an electron-attracting, oxygen-containing group that bonds to the boron atom. The listed compounds (lithium-boron disalicylate and a special imide salt) exhibit the disadvantages already mentioned above however.

The compound lithium-bis(oxalato)borate (LOB) described for the first time in DE 19829030 is the first boron-centred complex salt described for use as an electrolyte that employs a dicarboxylic acid (in this case oxalic acid) as chelate component. The compound is simple to produce, non-toxic and electrochemically stable up to about 4.5 V, which permits its use in lithium ion batteries. A disadvantage however is that it can hardly be used in new battery systems with cell voltages of >3 V. For such electrochemical storage units salts with stabilities of ≧ca. 5 V are required. A further disadvantage is that lithium-bis(oxalato)borate does not allow any possible structural variations without destroying the basic chemical framework.

In EP 1035612 additives inter alia of the formula

are mentioned,
and m and p=0, 1, 2, 3 or 4, where m+p=4, and
$R^1$ and $R^2$ are identical or different and are optionally directly bonded to one another by a single or double bond, in each case individually or jointly denote an aromatic or aliphatic carboxylic acid or sulfonic acid, or in each case individually or jointly denote an aromatic ring from the group comprising phenyl, naphthyl, anthracenyl or phenanthrenyl, which may be unsubstituted or singly to quadruply substituted by A or Hal, or in each case individually or jointly denote a heterocyclic aromatic ring from the group comprising pyridyl, pyrazyl or bipyridyl, which may be singly to triply unsubstituted or substituted by A or Hal, or in each case individually or jointly denote an aromatic hydroxy acid from the group comprising aromatic hydroxycarboxylic acids or aromatic hydroxysulfonic acids, which may be singly to quadruply unsubstituted or substituted by A or Hal, and
Hal=F, Cl or Br, and
A=alkyl radical with 1 to 6 C atoms, which may be singly to triply halogenated.

As particularly preferred additives there may be mentioned lithium-bis[1,2-benzenediolato(2-)O,O']borate(1-), lithium-bis[3-fluoro-1,2-benzenediolato(2-)O,O']borate(1-), lithium-bis[2,3-naphthalenediolato(2-)O,O']borate(1-), lithium-bis[2,2'-biphenyldiolato(2-)O,O']borate(1-), lithium-bis[salicylato(2-)O,O']borate(1-), lithium-bis[2-olatobenzenesulfonato(2-)O,O']borate(1-), lithium-bis[5-fluoro-2-olatobenzenesulfonato(2-)O,O']borate(1-), lithium phenolate and lithium-2,2-biphenolate. These are all symmetrical lithium chelatoborates of the type $Li[BL_2]$.

Lithium-bis(malonato)borate, which is said to have an electrochemical window up to 5 V, has been described by C.

Angell as being an electrochemically particularly stable simple lithium-(chelato)borate compound. The compound in question has the disadvantage however that it is practically insoluble in the usual battery solvents (e.g. only 0.08 molar in propylene carbonate), which means that it can be dissolved and characterised only in DMSO and similar prohibitive solvents for batteries (Wu Xu and C. Austen Angell, Electrochem. Solid-State Lett. 4, E1-E4, 2001).

Chelatoborates may furthermore be present in protonated form (i.e. $H[BL_2]$) where L is a bidentate ligand that is bound to the boron atom via two oxygen atoms. Such compounds have an extremely high acidic strength and may therefore be used as so-called super acids in organic synthesis as catalysts for cyclisations, aminations, etc. For example, hydrogen-bis (oxalato)borate has been proposed as a catalyst for the production of tocopherol (U.S. Pat. No. 5,886,196). The disadvantage of this catalyst however is the relatively poor hydrolytic stability.

The object of the present invention is to obviate the disadvantages of the prior art and in particular to provide substances for conducting salts that can be produced relatively simply and inexpensively from commercially available raw materials, that have a sufficient oxidation stability of at least 4.5 V, and that are readily soluble in conventionally used "battery solvents". Furthermore the substances should be relatively resistant to decomposition by water or alcohols.

This object is achieved by "mixed" boron chelate complexes of the general formula

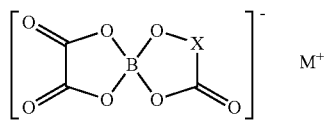

where
X is either —$C(R^1R^2)$— or —$C(R^1R^2)$—$C(=O)$—, in which
$R^1$, $R^2$ independently of one another denote H, alkyl (with 1 to 5 C atoms), aryl, silyl or a polymer, and one of the alkyl radicals $R^1$ or $R^2$ may be bonded to a further chelatoborate radical,
or X denotes 1,2-aryl with up to two substituents S in the positions 3 to 6

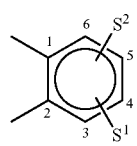

in which $S^1$, $S^2$ independently of one another denote alkyl (with 1 to 5 C atoms), fluorine or a polymer,
as well as M+ denotes $Li^+$, $Na^+$, $K^+$, $Rb^+$, $Cs^+$ or $[(R^3R^4R^5R^6)N]^+$ or $H^+$, where $R^3$, $R^4$, $R^5$, $R^6$ independently of one another denote H or alkyl with preferably 1 to 4 C atoms.

It has surprisingly been found that the aforelisted borates having two different ligands, one of which is the oxalato radical, have significantly better solubilities than the symmetrical comparison compounds.

The following compounds are preferred: hydrogen-(malonato,oxalato)borate (HMOB), hydrogen-(glycolato,oxalato)borate (HGOB), hydrogen-(lactato,oxalato)borate (HLOB), hydrogen-(oxalato, salicylato)borate (HOSB) and bis-[hydrogen-(oxalato,tartrato)borate] (BHOTB), as well as the lithium, caesium and tetraalkylammonium salts of the aforementioned acids.

The solubility of the mixed borates, which is better compared with that of the symmetrical comparison compounds, is demonstrated in Table 1 by the example of the lithium compounds:

TABLE 1

Solubilities of various lithium borate complex salts (in mole/kg) at room temperature

|  | LOB | LLB | LMB | LOMB | LLOB | LOSB |
|---|---|---|---|---|---|---|
| THF | 1.90 | <0.01 | 0.09 | 0.17 | 1.59 | 1.21 |
| PC | 0.88 | <0.01 | 0.02 | 0.17 | 0.17 | 1.50 |
| γ-BL | 1.55 | 0.02 | 0.13 | 0.62 | 0.96 | 0.98 |
| 1,2-DME | 1.30 | <0.01 | 0.003 | 0.20 | 0.93 | 0.43 |
| Acetone | 1.82 | <0.01 | 0.03 | 0.43 | 1.38 | 0.51 |

LOB = Lithium-bis(oxalato)borate
LLB = Lithium-bis(lactato)borate
LMB = Lithium-bis(malonato)borate
LOMB = Lithium-(malonato,oxalato)borate
LLOB = Lithium-(lactato,oxalato)borate
LOSB = Lithium-(oxalato,salicylato)borate
THF = Tetrahydrofuran
PC = Propylene carbonate
γ-BL = γ-Butyrolactone
1,2-DME = 1,2-dimethoxyethane It is clear that the compound LOB not according to the invention has in most cases the best solubility. Surprising however compared to the other symmetrical compounds (LMB and LLB) is the substantially improved solubility of the mixed chelatoborates. In the solvent propylene carbonate the mixed LOSB is even substantially more soluble than LOB.

Table 2 shows the hydrolysis susceptibility of various chelatoborates.

TABLE 2

Degree of hydrolysis of 5% solutions in water after stirring for 2 hours at room temperature

|  | LOB | LMB | LMOB |
|---|---|---|---|
| Degree of hydrolysis (%) | >50 | 5 | 15 |

The metal salts with mixed boron chelate anions according to the invention can dissolve in relatively high concentrations in the typical aprotic solvents such as carbonates, lactones and ethers used for high-performance batteries. Table 3 gives the measured conductivities at room temperature:

TABLE 3

Conductivities of non-aqueous electrolytes with mixed chelatoborate salts in γ-BL, 1,2-DME and THF at room temperature

|  | γ-BL | | 1,2-DME | | THF | |
|---|---|---|---|---|---|---|
|  | Concn.[1] | Cond.[2] | Concn.[1] | Cond.[2] | Concn.[1] | Cond.[2] |
| LLOB | 0.96 | 2.61 | 0.93 | 6.52 | 1.59 | 2.91 |
| LSOB |  |  | 0.43 | 4.17 | 1.21 | 3.17 |
| LMOB | 0.54 | 3.59 |  |  | 0.17 | 0.41 |

TABLE 3-continued

Conductivities of non-aqueous electrolytes with
mixed chelatoborate salts in γ-BL, 1,2-DME and
THF at room temperature

| | γ-BL | | 1,2-DME | | THF | |
|---|---|---|---|---|---|---|
| | Concn.[1] | Cond.[2] | Concn.[1] | Cond.[2] | Concn.[1] | Cond.[2] |
| LMB | 0.13 | 1.65 | | | 0.009 | 0.01 |
| LLB | 0.02 | 0.01 | insoluble | 0 | insoluble | 0 |
| LOB | 1.04 | 6.96 | | | | |

[1] in mmole/g
[2] in mS/cm

It can be seen from Table 3 that solutions of the mixed borate salts have conductivities of >2 mS/cm necessary for the operation of lithium batteries. In contrast to this, the solutions not according to the invention of the symmetrically substituted salts LMB and LLB have significantly lower or practically zero conductivities.

The conductivities may be optimised corresponding to the prior art by for example combining at least one solvent having a high dielectric constant (for example ethylene carbonate, propylene carbonate) with at least one viscosity-reducing agent (for example dimethyl carbonate, butylacetate, 1,2-dimethoxyethane, 2-methyltetrahydro-furan).

The salts with mixed chelatoborate anions furthermore exhibit the desired high degree of electrochemical stability. For example the compound lithium-(lactato,oxalato)borate according to the invention has a so-called "electrochemical window" of ca. 5 V, i.e. it is stable in the range between 0 and ca. 5 V ($Li/Li^+=0$), as shown in FIG. 1.

The boron chelate complexes described above can be fixed to polymer compounds by known techniques. Thus, it is possible to remove the acidic hydrogen atoms in the α-position to the carbonyl groups by means of suitable bases and to add the carbanionic species obtained in this way to functionalised (e.g. halogenated) polymers.

The boron chelate complexes according to the invention can be produced by reacting boric acid or boron oxide with oxalic acid and the other chelate-forming agent, optionally in the presence of an oxidic metal source (e.g. $Li_2CO_3$, NaOH, $K_2O$) or an ammonium salt, for example according to the following equations:

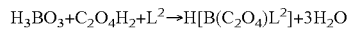

or

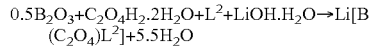

where $L^2$ denotes dicarboxylic acid (not oxalic acid), hydroxycarboxylic acid or salicylic acid (which may be at most doubly substituted).

Preferably stoichiometric amounts of the starting substances are used, i.e. the molar ratio boron/oxalic acid/chelate-forming agent $L^2$/optionally oxidic metal source or ammonium salt is about 1:1:1:1. Small deviations from the theoretical stoichiometry (e.g. 10% above or below) are possible without having a marked effect on the chelatoborate end product. Thus, if one of the ligands is present in excess, the corresponding symmetrical end product will occur to a greater extent in the reaction mixture. Thus for example if >1 mole of oxalic acid is used per equivalent of boron-containing raw material, then bis-(oxalato)borate will be formed in significant amounts. If the reaction is carried out in the presence of an oxidic lithium raw material LOB is formed, which in combination with the mixed chelatoborates according to the invention does not interfere in applications as a battery electrolyte. If on the other hand an acid $L^2$ whose symmetrical chelato compound is sparingly soluble is employed in excess, then the byproduct $M[B(L^2)_2]$ can easily be separated by a simple dissolution/filtration step. It is important to use ca. 2 moles of chelate-forming agent per equivalent of boron component. If the chelate-forming agent is not used in a stoichiometric amount, unreacted boron component or undesirable 1:1-adduct ($HO—B(C_2O_4)$ or $HO-BL^2$) will remain. If more than 2 moles of chelate-forming agent are used, then unreacted chelate-forming agent will remain, which has to be separated in a complicated procedure.

The reaction according to the above chemical equations is preferably carried out by suspending the raw material components in a medium suitable for the azeotropic removal of water (e.g. toluene, xylene, methylcyclohexane, perfluorinated hydrocarbons with more than 6 C atoms) and removing the water azeotropically in a known way.

It is also possible to carry out the synthesis in aqueous solution. In this case the components are added to water in an arbitrary sequence and are concentrated by evaporation while stirring, preferably under reduced pressure. After removing most of the water a solid reaction product forms which, depending on the specific product properties, is finally dried at temperatures between 100° and 180° C. and under reduced pressure (e.g. 10 mbar). Apart from water, alcohols and other polar organic solvents are also suitable as reaction media.

Finally, the product can also be produced without adding any solvent, i.e. the commercially available raw materials are mixed and then heated by supplying heat and dehydrated preferably under reduced pressure.

The acids $H[BC_2O_4L^2]$ produced in this way are used in organic synthesis as super acid catalysts, e.g. for condensations, hydroaminations or debenzylations. Lithium salts of the mixed chelatoborates are used as electrolytes in galvanic cells, preferably lithium batteries. The ammonium and caesium salts may be used in electrolytic double-layer capacitors.

BRIEF DESCRIPTION OF THE FIGURE

FIG. 1 shows Cyclovoltammogram of a 0.5 molar solution of lithium-(lactato,oxalato)-borate (LLOB) in γ-butyrolactone against nickel electrodes.

DETAILED DESCRIPTION OF THE INVENTION

The invention is described in more detail hereinafter with the aid of the following examples.

Example 1

Production of Lithium-(lactato,oxalato)borate (LLOB) by Means of Azeotropic Drying 100.9 g of a 72.0% aqueous lactic acid solution (801 mmoles), 49.59 g of boric acid (802 mmoles) and 100.9 g of oxalic acid dihydrate (800 mmoles) were suspended in 300 ml (ca. 270 g) of toluene in an inert (i.e. dried and filled with argon as protective gas) 1 l capacity double-jacket reactor equipped with cooler, Dean-Stark water separator, stirrer and thermometer. A total of 30.87 g (418 mmoles) of pure lithium carbonate were then carefully added in portions from a metering valve while stirring thoroughly. This resulted in a vigorous formation of gas and foam. The solids agglomerated to form a viscous paste, which however could be suspended by stirring vigorously.

After the formation of foam had stopped the temperature of the heating oil was raised to 130° C. within about 1 hour. The azeotropically formed water was removed in portions. After a total of 10 hours' refluxing a total of 96.7 g of water had been separated.

The reaction mixture was cooled to 40° C. and poured onto a glass frit and filtered. The colourless solids were washed twice with toluene and once with pentane.

The finely powdered product was dried first of all at room temperature and then at 100° C. on a rotary evaporator.

Yield: 150.8 g (=97% of theory)
Analysis:

|    | Actual | Theoretical |
|----|--------|-------------|
| Li | 5.05   | 5.16        |
| B  | 4.9    | 5.16        |

$\delta^{11}$B (DMF): 8.8 ppm; in addition a very small amount (<5%) of byproducts with boron shifts at 10.1 and 7.5 ppm.

Thermogravimetry (TGA): decomposition starts at ca. 270° C.

Example 2

Production of lithium-(oxalato,salicylato)borate (LOSB) by Means of Azeotropic Drying 49.59 g of boric acid, 100.9 g of oxalic acid dihydrate and 110.45 g of salicylic acid were suspended in 400 ml of xylene in the apparatus described in Example 1, 30.9 g of lithium carbonate were added in portions, and the whole was then refluxed for 6 hours. During this time 78 g of water were separated.

The reaction mixture was cooled to 50° C., filtered and the insoluble colourless solid was washed with xylene and then with hexane. A colourless powder was obtained after drying at room temperature under an oil pump vacuum:

Yield: 183.5 g (95% of theory)
$\delta^{11}$B (DMF): 5.5 ppm; (in addition impurities at 7.4 ppm (LOB, ca. 10%) and 3.8 (LSB, ca. 13%)
TGA: decomposition starts at ca. 210° C.

The crude product was purified by recrystallisation in THF/diethyl ether.

Example 3

Production of hydrogen-(salicylato, oxalato)borate (HSOB) by Total Concentration by Evaporation on a Rotary Evaporator 61.8 g of boric acid, 138.1 g of salicylic acid and 126.1 g of oxalic acid dihydrate (in each case 1 mole) were mixed in a 1 capacity round bottom flask and heated on a rotary evaporator at only slightly reduced pressure (900 mbar) at 110° to 115° C. After about 15 minutes the reaction mixture fully melted and water began to distil off. After a further 30 minutes the pressure was reduced further, whereupon the mixture boiled vigorously. Towards the end of the separation of the water (after about 2 hours counting from the start of the reaction) the reaction mass solidified at a pressure of 20 to 30 mbar and an oil bath temperature of 125° C. into hard, in some cases coloured, lumps. Small amounts (a few g) of a colourless, needle-shaped sublimate, which was identified as salicylic acid, were also observed.

The reaction mass was cooled and ground by means of a pestle and mortar. The now white, powdery reaction material was again dried to constant weight on a rotary evaporator at 115° to 125° C. and finally 10 mbar (2 hours).

Yield: 216 g (92%) of almost colourless powder

The product was extremely soluble in propylene carbonate, γ-butyrolactone, 1,2-dimethyoxyethane, acetone and dimethylformamide.

$\delta^{11}$B (1,2-DME): 5.5 ppm (main product) 7.6 ppm (HOB, ca. 15%) 3.5 ppm (hydrogen-bis(salicylato)borate, ca. 10%)

The crude product was purified by recrystallisation from acetone/MTBE.

The invention claimed is:

1. A boron chelate complex of the formula

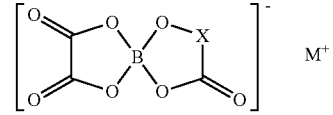

wherein X is either —C(R$^1$R$^2$)— or —C(R$^1$R$^2$)—C(=O)—, wherein R$^1$ and R$^2$ are independently selected from the group consisting of H, C$_1$-C$_5$ alkyl, aryl, silyl and a polymer, wherein if R$^1$ or R$^2$ are alkyl, they may be bonded to a chelatoborate radical, or wherein X is a 1,2-aryl with up to two substituents S in the positions 3 to 6 of the formula

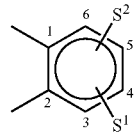

in which S$^1$ and S$^2$ are independently selected from the group consisting of a C$_2$ to C$_5$ alkyl, fluorine and a and polymer; wherein M+ is selected from the group consisting of Li$^+$, Na$^+$, K$^+$, Rb$^+$, Cs$^+$, [(R$^3$R$^4$R$^5$R$^6$)N]$^+$ and H$^+$, wherein R$^3$, R$^4$, R$^5$, and R$^6$ are independently H or alkyl, wherein if X is —C(R$^1$R$^2$)—C(=)—, at least one of R$^1$ and R$^2$ are not H.

2. A boron chelate complex according to claim 1, wherein the boron chelate complex is selected from the group consisting of hydrogen-(malonato, oxalato) borate, hydrogen-(glycolato, oxalato) borate, hydrogen-(lactato, oxalato) borate, hydrogen-(oxalato, salicylato) borate, bis-[hydrogen-(oxalato, tartrato) borate, or a lithium, caesium or tetraalkylammonium salt of the boron chelate complex.

3. A boron chelate complex according to claim 1, wherein the boron chelate complex is hydrogen-(malonato, oxalato) borate.

4. A boron chelate complex according to claim 1, wherein the boron chelate complex is hydrogen-(lactato, oxalato) borate.

5. A boron chelate complex according to claim 1, wherein the boron chelate complex is hydrogen-(oxalato, salicylato) borate.

6. A boron chelate complex according to claim 1, wherein the boron chelate complex is bis-[hydrogen-(oxalato, tartrato) borate.

7. A boron chelate complex according to claim 1, wherein M$^+$ is lithium.

8. A boron chelate complex according to claim 1, wherein M⁺ is cesium.

9. A boron chelate complex according to claim 1, wherein M⁺ is [(R³R⁴R⁵R⁶)N]⁺.

10. A boron chelate complex according to claim 1, wherein M⁺ is Na⁺.

11. A boron chelate complex according to claim 1, wherein M⁺ is K⁺.

12. A boron chelate complex according to claim 1, wherein M⁺ is Rb⁺.

13. A boron chelate complex according to claim 1, wherein X is —C(R¹R²)—.

14. A boron chelate complex according to claim 1, wherein X is —C(R¹R²)—C(=O)—.

15. A boron chelate complex according to claim 1, wherein X is the 1,2-aryl with up to two substituents S in the positions 3 to 6 of the formula

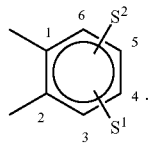

* * * * *